(12) United States Patent  (10) Patent No.: US 7,670,373 B1
Sabanathan  (45) Date of Patent: Mar. 2, 2010

(54) OCCLUSION DEVICE

(75) Inventor: Sabaratnam Sabanathan, Leeds (GB); Thirumani Sabanathan, legal representative, Leeds (GB)

(73) Assignee: Pulmonx Corporation, Redwood City, CA (US)

( * ) Notice: Subject to any disclaimer, the term of this patent is extended or adjusted under 35 U.S.C. 154(b) by 0 days.

(21) Appl. No.: 09/762,692

(22) PCT Filed: Mar. 3, 1998

(86) PCT No.: PCT/GB98/00652

§ 371 (c)(1),
(2), (4) Date: Oct. 31, 2005

(87) PCT Pub. No.: WO98/48706

PCT Pub. Date: Nov. 5, 1998

(30) Foreign Application Priority Data

Apr. 30, 1997 (GB) .................. 9708681.3

(51) Int. Cl.
A61F 2/20 (2006.01)
A61M 16/00 (2006.01)
(52) U.S. Cl. ..................... 623/9; 128/207.15
(58) Field of Classification Search ............ 128/207.15; 606/157, 158; 623/2.26, 2.27, 2.34, 9, 11.11; 424/422, 423, 434, 489
See application file for complete search history.

(56) References Cited

U.S. PATENT DOCUMENTS 2,832,078 A  4/1958  Williams ................ 623/219
2,981,254 A  4/1961  Vanderbilt .............. 128/350
3,320,972 A  5/1967  High et al. .............. 137/844
3,445,916 A  5/1969  Schulte .................. 294/58

(Continued)

FOREIGN PATENT DOCUMENTS

DE  9205797  6/1992

(Continued)

OTHER PUBLICATIONS

Sat Sharma. Pulmonary Arteriovenous Fistulae. Jul. 2006 emedicine.com.*

(Continued)

Primary Examiner—Justine R Yu
Assistant Examiner—Kristen C Matter
(74) Attorney, Agent, or Firm—Townsend and Townsend and Crew LLP

(57) ABSTRACT

An obturator for a bronchial tube or tubule of a human or animal lung comprises a blocking element (92) and a securing element (90). The blocking element serves to seal the tube or tubule against the passage of fluid past the obturator when the obturator is disposed in a bronchial tube or tubule. The securing element serves to retain the blocking element in position. The blocking element comprises a substantially cylindrical plug of biocompatible, resiliently deformable closed-cell foamed plastics material, such as PVC. The securing element comprises a stent having barbs (98) to engage and retain the blocking element. The stent also has anchors (100) to retain the stent in a bronchial tube or tubule. A method of treatment of emphysema or other lung conditions or diseases in human or animal patients comprises placing an obturator in a bronchial tube or tubule of the patient so as to seal the tube or tubule against the passage of fluid past the obturator.

16 Claims, 3 Drawing Sheets

U.S. PATENT DOCUMENTS

| Patent No. | | Date | Inventor | Class |
|---|---|---|---|---|
| 3,657,744 | A | 4/1972 | Ersek | 128/334 |
| 3,671,979 | A | 6/1972 | Moulopoulos | 623/211 |
| 3,788,327 | A | 1/1974 | Donowitz et al. | 128/350 |
| 3,874,388 | A | 4/1975 | King et al. | 128/334 |
| 4,014,318 | A | 3/1977 | Dockum et al. | 128/1 |
| 4,056,854 | A | 11/1977 | Boretos et al. | 623/218 |
| 4,084,268 | A | 4/1978 | Ionescu et al. | 623/215 |
| 4,086,665 | A | 5/1978 | Poirier | 623/1 |
| 4,212,463 | A | 7/1980 | Repinski et al. | 273/418 |
| 4,218,782 | A | 8/1980 | Rygg | 623/215 |
| 4,222,126 | A | 9/1980 | Boretos et al. | 623/219 |
| 4,250,873 | A | 2/1981 | Bonnet | 600/104 |
| 4,302,854 | A | 12/1981 | Runge | 3/1.7 |
| 4,339,831 | A | 7/1982 | Johnson | 623/218 |
| 4,477,930 | A | 10/1984 | Totten et al. | 3/1.5 |
| 4,710,192 | A | 12/1987 | Liota et al. | |
| 4,732,152 | A | 3/1988 | Wallsten et al. | 128/343 |
| 4,759,758 | A | 7/1988 | Gabbay | 623/2 |
| 4,774,942 | A | 10/1988 | Moellers | 128/205.24 |
| 4,808,183 | A | 2/1989 | Panje | 623/9 |
| 4,819,664 | A | 4/1989 | Nazari | 128/207.15 |
| 4,830,003 | A | 5/1989 | Wolff et al. | 128/343 |
| 4,832,680 | A | 5/1989 | Haber et al. | 600/31 |
| 4,846,836 | A | 7/1989 | Reich | 623/11 |
| 4,850,999 | A | 7/1989 | Planck | 623/1 |
| 4,877,025 | A | 10/1989 | Hanson | 128/107.16 |
| 4,879,998 | A | 11/1989 | Moellers | 128/205.4 |
| 4,934,999 | A | 6/1990 | Bader | 600/29 |
| 4,946,463 | A * | 8/1990 | Wright | 606/158 |
| 4,968,294 | A | 11/1990 | Salama | 600/30 |
| 4,983,177 | A * | 1/1991 | Wolf | 606/157 |
| 4,990,151 | A | 2/1991 | Wallstén | 606/108 |
| 4,994,069 | A * | 2/1991 | Ritchart et al. | 606/191 |
| 5,061,274 | A | 10/1991 | Kensey | 606/213 |
| 5,116,360 | A | 5/1992 | Pinchuk et al. | 623/1 |
| 5,116,564 | A | 5/1992 | Jansen | 264/255 |
| 5,123,919 | A | 6/1992 | Sauter et al. | 623/2 |
| 5,147,370 | A * | 9/1992 | McNamara et al. | 623/1.11 |
| 5,151,105 | A | 9/1992 | Kwan-Gett | 623/1 |
| 5,152,770 | A * | 10/1992 | Bengmark et al. | 606/157 |
| 5,158,548 | A | 10/1992 | Lau et al. | 604/96 |
| 5,161,524 | A | 11/1992 | Evans | 128/203.15 |
| 5,246,445 | A | 9/1993 | Yachia et al. | |
| 5,250,286 | A * | 10/1993 | Skupin | 424/45 |
| 5,306,234 | A | 4/1994 | Johnson | 604/49 |
| 5,352,240 | A | 10/1994 | Ross | 623/2 |
| 5,358,518 | A | 10/1994 | Camilli | 623/2 |
| 5,366,478 | A | 11/1994 | Brinkerhoff et al. | 660/213 |
| 5,382,261 | A | 1/1995 | Palmaz | |
| 5,392,775 | A | 2/1995 | Adkins et al. | 128/207.16 |
| 5,409,019 | A | 4/1995 | Wilk | 128/898 |
| 5,411,507 | A | 5/1995 | Heckele | 606/108 |
| 5,411,552 | A | 5/1995 | Anderson et al. | 623/2 |
| 5,413,599 | A | 5/1995 | Imachi et al. | 623/2 |
| 5,417,226 | A | 5/1995 | Juma | 128/885 |
| 5,445,626 | A | 8/1995 | Gigante | 604/349 |
| 5,453,090 | A | 9/1995 | Martinez et al. | 604/53 |
| 5,486,154 | A | 1/1996 | Kelleher | 600/104 |
| 5,499,995 | A | 3/1996 | Teirstein | 606/192 |
| 5,500,014 | A | 3/1996 | Quijano et al. | 623/2 |
| 5,562,608 | A | 10/1996 | Sekins et al. | 604/20 |
| 5,588,424 | A | 12/1996 | Insler et al. | 128/207.14 |
| 5,645,519 | A | 7/1997 | Lee et al. | 600/114 |
| 5,645,565 | A | 7/1997 | Rudd et al. | 606/213 |
| 5,649,906 | A | 7/1997 | Gory et al. | 606/108 |
| 5,658,330 | A * | 8/1997 | Carlisle et al. | 623/11.11 |
| 5,660,175 | A | 8/1997 | Dayal | 128/207.15 |
| 5,662,713 | A | 9/1997 | Anderson et al. | 623/12 |
| 5,683,451 | A | 11/1997 | Lenker et al. | 623/1 |
| 5,697,968 | A | 12/1997 | Rogers et al. | 623/1 |
| 5,755,770 | A | 5/1998 | Ravenscroft | 623/1 |
| 5,803,080 | A | 9/1998 | Freitag | 128/207.14 |
| 5,833,707 | A * | 11/1998 | McIntyre et al. | 606/198 |
| 5,840,081 | A | 11/1998 | Andersen et al. | 623/2 |
| 5,851,232 | A | 12/1998 | Lois | 623/1 |
| 5,853,422 | A * | 12/1998 | Huebsch et al. | 606/213 |
| 5,855,587 | A | 1/1999 | Hyon et al. | 606/188 |
| 5,855,601 | A | 1/1999 | Bessler et al. | 623/2 |
| 5,876,445 | A | 3/1999 | Anderson et al. | |
| 5,919,224 | A * | 7/1999 | Thompson et al. | 606/200 |
| 6,022,312 | A | 2/2000 | Chaussy et al. | 600/29 |
| 6,027,508 | A | 2/2000 | Ren et al. | 606/108 |
| 6,287,290 | B1 | 9/2001 | Perkins et al. | |
| 6,398,775 | B1 | 6/2002 | Perkins et al. | |
| 6,527,761 | B1 | 3/2003 | Soltesz et al. | |
| 6,585,639 | B1 | 7/2003 | Kotmel et al. | |
| 6,709,401 | B2 | 3/2004 | Perkins et al. | |
| 6,878,141 | B1 | 4/2005 | Perkins et al. | |
| 6,997,918 | B2 | 2/2006 | Soltesz et al. | |
| 2002/0062120 | A1 | 5/2002 | Perkins et al. | |
| 2002/0077593 | A1 | 6/2002 | Perkins et al. | |
| 2004/0158228 | A1 | 8/2004 | Perkins et al. | |
| 2005/0015106 | A1 | 1/2005 | Perkins et al. | |
| 2005/0061322 | A1 | 3/2005 | Freitag | |
| 2005/0203483 | A1 | 9/2005 | Perkins et al. | |

FOREIGN PATENT DOCUMENTS

| | | |
|---|---|---|
| DE | 4101936 | 7/1992 |
| EP | 204218 | 12/1986 |
| EP | 0621015 | 10/1994 |
| EP | 1 237 516 | 6/2006 |
| GB | 2324729 | 11/1998 |
| SU | 852321 | 8/1981 |
| SU | 1371700 | 2/1988 |
| SU | 1593651 | 9/1990 |
| WO | 94/26175 | 11/1994 |
| WO | 95/32018 | 11/1995 |
| WO | 96/34582 | 11/1996 |
| WO | 96/39960 | 12/1996 |
| WO | 98/48706 | 11/1998 |
| WO | 01/02042 | 1/2001 |
| WO | 02/094087 | 11/2002 |
| WO | 03/105941 | 12/2003 |
| WO | 2004/064885 | 8/2004 |

OTHER PUBLICATIONS

Auerbach et al. Localized pulmonary interstitial emphysema: treatment by bronchial occlusion. American Journal of Perintology, Oct. 1, 1983(1): 52-7.*

Lefrak et al. Recent advances in surgery for emphysema, Annual Review of Medicine 1997;48:387-98.*

Ponn et al. (Treatment of peripheral bronchopleural fistulas with endobronchial occlusion coils. Annals of Thoracic Surgery, Dec. 1993; 56(6): 1343-7).*

Al Jishi et al., "Selective Bronchial Occlusion for Treatment of Bullous Interstitial Emphysema and Bronchopleural Fistula." J. of Pediatric Surgery, 29:1545-1547, 1994.

Derwent# 007607249 WPI Acc. No. 1988-241181/198834 (citing Russian Application No. SU4026409, published Feb. 21, 1986), Russian Patent No. SU 1371700.

Derwent# 008650867 WPI Acc. No. 1991-154896/199121 (citing Russian Application No. SU4280143, published Jul. 7, 1987), Russian Patent No. SU 1593651.

Guyton, Arthur C., Textbook of Medical Physiology, 6$^{th}$ Edition, Philadelphia: W.B. Saunders Company, pp. 477, 496-498 (1981).

Harris et al., "The Experimental Production in Dogs of Emphysema with Associated Asthmatic Syndrome by Means of an Intratracheal Ball Valve", J. Lab. Clini. Med., 9(iv):75-88, 1919.

Lewis et al., "Pulmonary Interstitial Emphysema: Selective Broncial Occlusion with a Swan-Ganz Catheter", Archives of Disease in Childhood, 63:313-315, 1988.

Mathew et al., "Selective bronchial obstruction for treatment of bullous interstitial emphysema." J. of Ped., 96:475-477, 1980.

Okada et al., "Emergent Bronchofiberoptic Bronchial Occlusion for Intractable Pneumothorax with Severe Emphysema", *The Jap. J. of Thor. And Cardio. Sur.*, 46:1078-1081, 1998.

Perini et al., "Deformation and migration of Palmaz stents after placement in the tracheobronchial tree," J Vasc Interv Radiol. 10(2 Pt 1):209-15, 1999.

Puhakka et al., "Acute Bronchial Obstruction: An Experimental Rabbit Model Study", *Int. J. of Pediatric Otorhinolaryngology*, 18:107-118, 1989.

Snider et al., "The Definition of Emphysema: Report of the National Heart Lung and Blood Institute, Division of Lung Diseases Workshop," *Am. Rev. Respir. Dis.*, 132:182-185, 1985.

Woodring et al., "Pneumothorax ex Vacuo", *Chest*, 100:1102-1124, 1996.

Perini et al. "Deformation and migration of Palmaz stents after placement in tracheobronchial tree" *JVIR* 10(2):209-215 (1999).

Certified English Translation of USSR patent 852321, published Aug. 7, 1981, entitled "A Method of Treatment of Acute Purulent Diseases of the Lungs and Pleura in Children".

Certified English Translation of German patent G 92 05 797.7, published Jul. 30, 1993, entitled "Self-expanding mesh basket used to occlude human hollow organs".

Derwent# 004823036 (citing European Application No. EP 86106933, published May 22, 1986) of European Patent No. EP204218.

Derwent #009123698 (citing German Application No. DE 4101936, published Jan. 21, 1991) of German Patent No. DE 4101936.

\* cited by examiner

OCCLUSION DEVICE

The present invention relates to a device useful in the treatment of emphysema and other diseases or disorders of the human or animal lung.

Emphysema is a disease of the lung caused primarily by prolonged smoking, although not exclusively thereby. It is an unrelenting, intractable and debilitating process. Emphysema is defined as an abnormal permanent enlargement of the air spaces distal to the terminal bronchioles, accompanied by destruction of their walls without obvious fibrosis. In this context, destruction means non-uniformity in the pattern of respiratory airspace enlargement; orderly appearance of the acinus is disturbed and may be lost.

Emphysema causes a physiological loss of lung elastic recoil, which decreases expiratory airflow by loss of driving pressure and premature airway closure from reduced airway traction. The effect of this is that the alveoli become hyper-inflated without there being any real exchange of air with the outside. Therefore the patient begins to feel starved of oxygen and so attempts to breathe more deeply. In breathing more deeply, the effects are exacerbated.

Not only are those individual alveoli which have a block in their respective bronchial tubules affected, but also neighbouring alveoli, perhaps in other regions of the lung, which may otherwise be perfectly serviceable, become affected because the hyper-inflated alveoli pressurise neighbouring alveoli and prevent them from expanding fully. There is, of course, a relatively fixed "exchange" volume of an individual's lung, that is to say, the difference between the expanded volume and the deflated volume. Emphysema reduces the exchange volume because undeflated alveoli occupy that space. Consequently, the only recourse available to the patient is to increase the expanded volume, thereby resulting in the barrel chest symptomatic of emphysema sufferers.

The major therapeutic modalities currently available consist of bronchodilator and anti-inflammatory drugs, directed at decreasing airway resistance, and antibiotics to treat acute and chronic infection. Supplemental oxygen therapy for the hypoxaemic patient improves exercise performance and improves survival in patients with cor pulmonale. Despite all available medical therapies, the course of the disease is one of progressive limitation, increasing dyspnoea and significant increase in overall mortality.

It has long been realised that full lung volume is more than enough for survival in most circumstances and that a person can survive quite satisfactorily with only one lung, for example. Heterogenous distribution of emphysema, together with the lack of pulmonary blood flow to those areas have made lung volume reduction surgery a logical option. Removal of parts of the lung affected by emphysema permits unaffected areas to become operative again and so enable a better quality of life for the patient. Clearly, however, such invasive procedures are of a very serious nature and some patients will not, in any event, be in a sufficiently strong condition to accept the trauma of such procedures. Primarily, the basic relief for emphysema sufferers is inactivity, on the one hand, and breathing pure oxygen, on the other.

Emphysema is a distressing condition affecting a relatively large proportion of the population, and a more effective and less traumatic treatment is required.

On a different matter, other lung conditions sometimes lead to bleeding into the lung. A patient having this condition feels movement of the blood caused by airflow in the lung during breathing, and perceives the blood as a foreign body and irritant. The patient coughs in an attempt to dislodge the perceived foreign body. Coughing blood, of course, is sometimes the first warning of a more serious disease or condition, but once that is realised, there is no benefit in such bleeding. Moreover, in such conditions where the lung might heal itself and subsequently stop bleeding, or indeed simply where the bleeding needs to be confined, the coughing reaction, which is almost impossible to resist, does not help the situation at all, and merely spreads the blood to other areas of the lung.

U.S. Pat. No. 5,382,261 discloses a vessel occluder for providing permanent occlusion of a vessel person by use of a flexible closure member attached to at least one radially expandable stent. The occluder does not have barbs or anchors or a stent.

DE-U-9205797 discloses a self expanding 'meshbasket' for the occlusion of human hollow organs. The invention is directed to female contraceptive devices and addresses the problem of remaining in place. The device may also find application in embolism therapy and vascular occlusion.

WO-A-9532018 discloses a body passageway closure for use in the occlusion of various passageways within the body, with particular application for the occlusion of blood vessels.

Therefore it is an object of the present invention to provide a method of treatment of certain lung conditions or diseases and to provide a device for such treatment.

In accordance with a first aspect of the present invention there is provided a method of treatment of emphysema or other lung conditions or diseases, the method comprising placing an obturator in a bronchial tube or tubule so as to seal the tube or tubule against the passage of fluid past the obturator.

In the case of emphysema, and by the simple expedient of inserting an obturator in a bronchial tube, a section of a lung can be isolated so that no air can be drawn into it. Thereafter, the isolated part deflates in time as the air remaining in it becomes absorbed, and so that part of the lung stops affecting other areas of the lungs, which can thus perform normally. Such a procedure is relatively simple, requiring only a delivery device for the obturator, which device is inserted through the mouth and airway of the patient until the proposed placement site is reached, whereupon the device is activated to release the obturator from the device.

In the case of bleeding into the lung, an obturator stops the flow of blood. The lung is tamponated by the obturator and blood merely collects in the isolated part of the lung and ultimately, if the bleeding stops, will be reabsorbed. Alternatively, in the case of some, perhaps terminal, conditions such as some lung cancers, it at least provides temporary relief for the patient.

In accordance with a second aspect of the invention there is provided the use of a blocking element and a securing element in the manufacture of an obturator for use in the treatment of a lung condition in a human or animal by blocking a bronchial tube or tubule. The condition may be emphysema.

Preferably the two elements are separate components, the blocking element serving to seal the tube or tubule against the passage of fluid past the obturator when the obturator is disposed in a bronchial tube or tubule, and the securing element serving to retain the blocking element in position in the tube or tubule.

The blocking element preferably comprises a substantially cylindrical plug of biocompatible material. The plug may comprise resiliently deformable closed-cell foamed plastics material, such as PVC, so that it may be compressed to facilitate insertion into the tube or tubule and thereafter expand to fill the cross-section of the tube or tubule.

It is known to employ stents in medical fields to expand and support collapsed blood vessels, and indeed bronchial tubes. A stent is a compressible framework which, when inserted into a vessel and released, expands and, within the limits of its expansion, supports and possibly expands the walls of the vessel.

Preferably, the securing element comprises a stent. The stent may have barbs to engage and retain the blocking element. The stent preferably also has anchors to retain the stent in a bronchial tube or tubule.

In one embodiment, the stent comprises a crown of surgical quality steel wire legs in zig-zag formation. Said barbs and anchors may depend from points of the crown. Preferably the crown is closed in its circumference, although this is not essential.

In another embodiment, the stent comprises a dome of surgical quality steel wire legs. Said barbs and anchors may be formed on the ends of said legs.

It is known in medical fields to block blood vessels, for example where a genetic or other defect has resulted in a hole which needs blocking, or, for example, in the case of babies whose aortic to pulmonary artery connection has not closed following birth, a condition known as patent ductus arteriosus. In the case of holes, it is well known to employ an "umbrella", where a diaphragm of material forms the seal against the blood vessel wall, the handle of the umbrella serving to keep the diaphragm across the vessel. In the case of babies, it has also been known to employ a plug of PVC foam to treat patent ductus arteriosus, the plug encouraging clotting.

However, in the case of bronchial tubes and tubules a diaphragm seal has not been used yet, although its application cannot be entirely ruled out. For example, an umbrella device with a larger surface area of contact with the bronchial mucosa might be as effective.

In blood vessels a complete seal is seldom required because any leak soon blocks by the formation of a clot; something that would not happen in an airway of a lung. Secondly, airways are not always absolutely circular in section, so a circular diaphragm may not always make a good seal, at least around some parts of the circumference, unless it has capacity to expand in all radial directions and has a large contact area.

However, a complete seal is an absolute requirement of the present invention (at least over the period of a single breath), because without it, air can leak past during inhalation and pressurise the lung in just the same way, and perhaps even to a greater extent. More importantly, however, a patient with such an obturator in place can only feel its presence if there is movement of air around it to stimulate adjacent nerve endings. Once a patient can feel the obturator, there will be irresistible compulsion to cough which, if done excessively, may be sufficient to dislodge the obturator.

Thus it has been found that a very effective seal is achieved by the use of said cylindrical plug of foamed PVC (of the type commonly employed as earplugs). The effectiveness of this arrangement is probably due to the fact that any leakage path has to be a long one and there are thus numerous opportunities for it to close and seal about at least one closed circuit: around the plug. Another reason is that a plug can mould itself to the shape of the tube or tubule, which is itself unlikely to be cylindrical, or, indeed, circular in cross-section.

Preferably, the method of the present invention employs an obturator of the type defined above.

The delivery device preferably comprises a delivery tube in which the obturator is received in a compressed state at a distal end thereof, a guide tube, which is capable of following a possibly tortuous path under the guidance of a surgeon from entry into the mouth of a patient, down the patient's trachea and one bronchus to a proposed delivery site in a bronchial tube or tubule, and which has a passage to receive the delivery tube therealong, and release means to eject the obturator from the delivery tube and guide tube.

The obturator needs to slide in the delivery tube during ejection and the stent provides a low friction surface of the obturator to facilitate such ejection.

It is feasible that the blocking and securing elements may be integrally formed from plastics material, and wherein the securing element comprises adhered or fused anchor elements on the blocking element.

It is also feasible that the securing element may comprise a memory metal which is released to its normal expanded shape by a physical parameter, for example, the passage of an electric current therethrough, once it has been inserted at the proposed location. Otherwise it is in the same form as the above described steel stent which relies on resilience for its expansion. The advantage of a memory metal device is that it requires no compression during insertion so that the delivery tube of the delivery device may be replaced by a simple guide rod to which it is connected.

The invention will be better understood from the following description of particular embodiments given as non-limiting examples. The description refers to the accompanying drawings, in which.

Figure 3A:
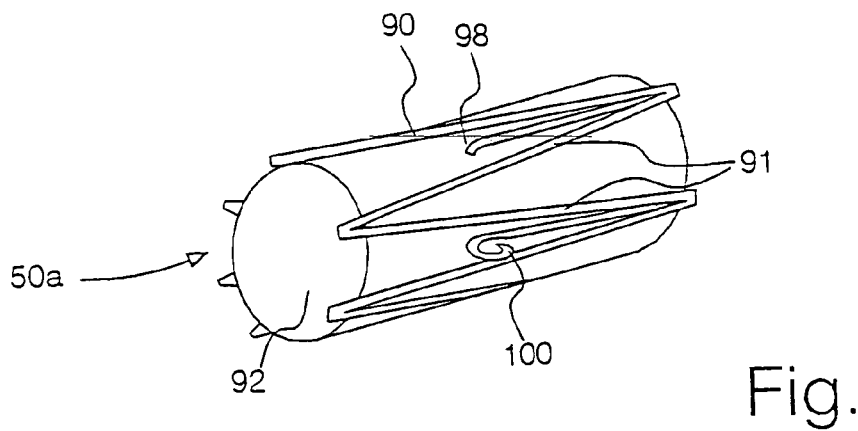
Figure 3B:
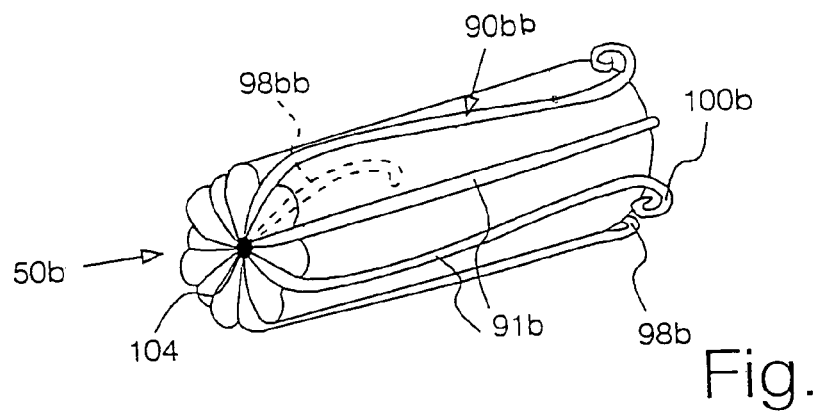
Figure 3C:
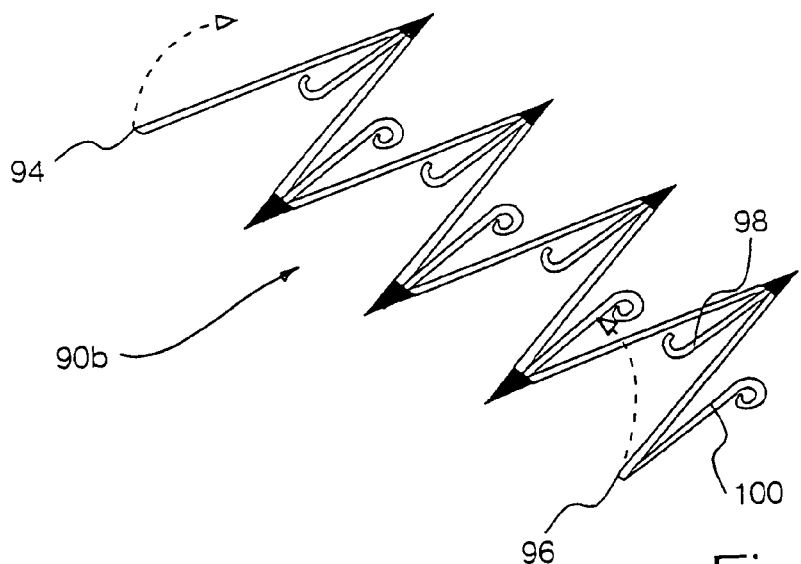
Figures 4A, 4B:
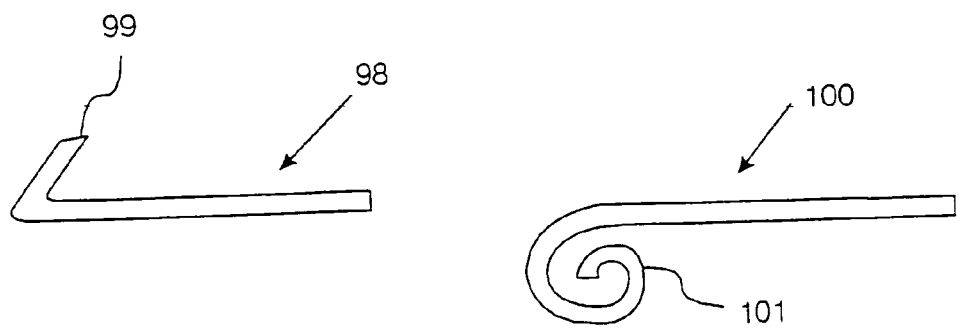
Figure 5:
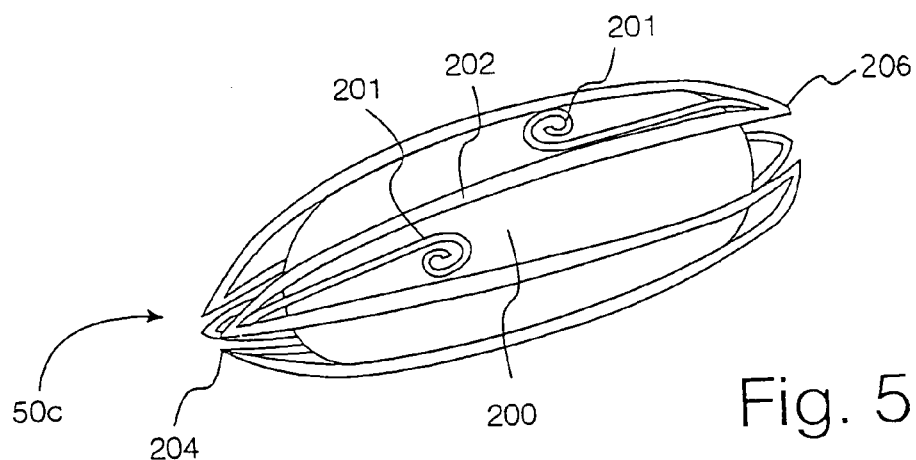
Figure 6:
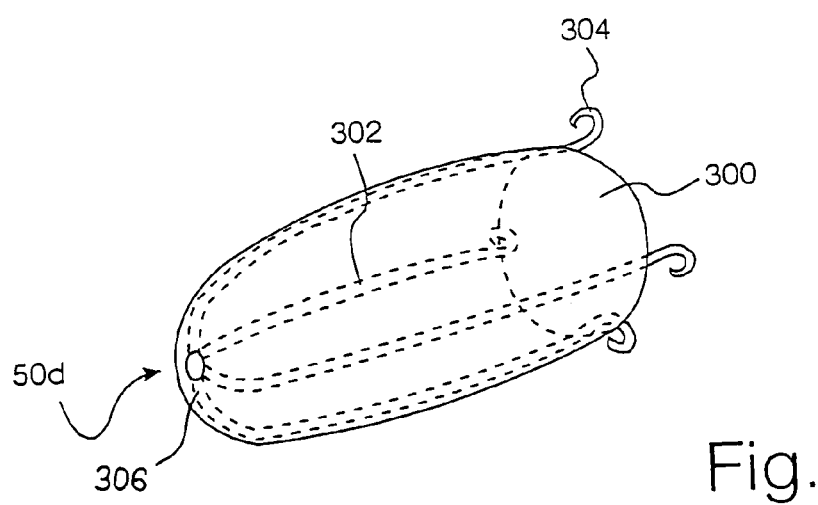

FIGS. 3a b and c show in perspective two embodiments of an obturator according to the present invention, that of FIG. 3a having a crown stent, and that of FIG. 3b having a dome stent, FIG. 3c being a crown stent an open configuration prior to rolling and, optionally, welding into a ring as in FIG. 3a;

FIGS. 4a and b show an internal barb and external anchor respectively;

FIG. 5 is a perspective view of another embodiment of obturator in accordance with the present invention; and, FIG. 6 is a perspective view of yet another embodiment of obturator also in accordance with the, present invention.

Figure 1:
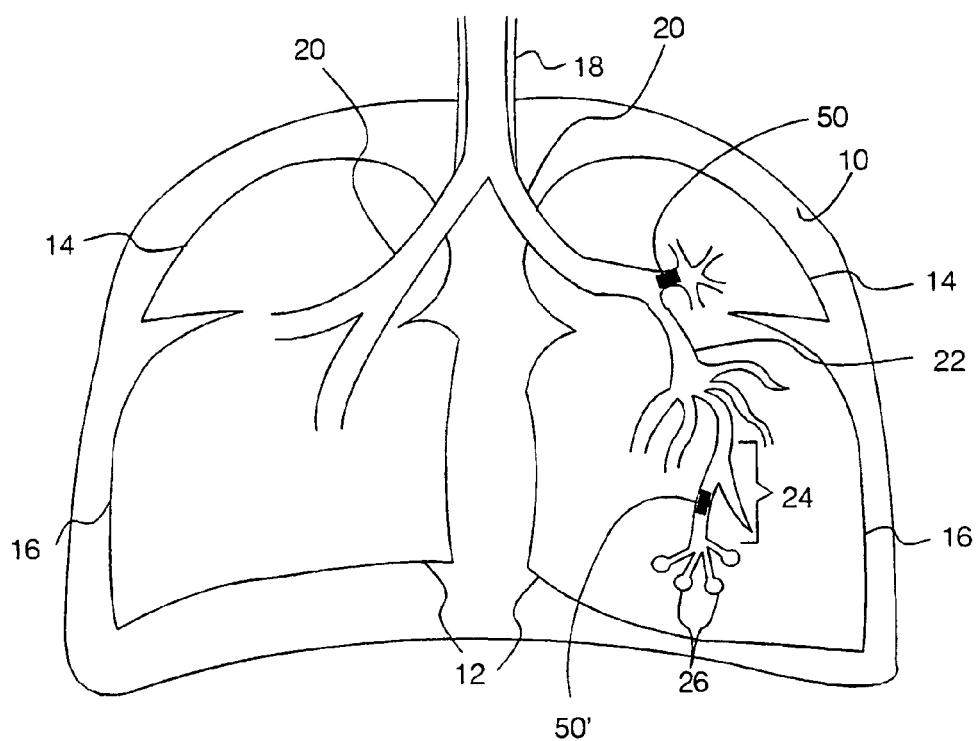
FIG. 1 shows a section through the human chest indicating the location of bronchial obturators in the lungs.

In FIG. 1 of the drawings, a human chest cavity 10 includes a pair of lungs 12 which each comprise upper and lower lobes 14, 16. A trachea 18 branches into two bronchi 20, which further branch into bronchial tubes 22 and segmental bronchi 24. The bronchi 24, after further branching, terminate in alveoli 26.

In the majority of patients suffering from emphysema, it frequently effects mainly the upper lobes 14 of the lungs, leaving the lower lobes 16 unaffected, or at least less affected. However, if no treatment is given to a patient, the expansion effect of the upper lobes as the condition develops presses on the lower lobes and reduces their capacity to perform efficiently. Lower lobe emphysema does occur in some patients, and in which event it is then the upper lobes which are compressed.

Thus the present invention suggests placing an obturator 50 in a bronchial tube or tubule to isolate the region of the lung supplied by that tube or tubule. Where the obturator is placed will be decided by the surgeon and will depend on the how localised the damaged region of lung is. That is to say, if the whole lobe is badly affected, then the obturator is placed in the lobar bronchus 22 supplying that lobe (as shown at 50 in FIG. 1). On the other hand, if the damage is more localised, then the obturator will be placed in a smaller segmental bronchus 24, (as shown at 50' in FIG. 1). Thus more than one obturator may be employed in the same pair of lungs isolating different regions of them. They will also be of different sizes, depending where they are to be inserted.

The above considerations equally apply when the condition being treated is not emphysema but some other condition which a doctor considers can usefully be treated by the method of the present invention. Such another condition is where a lung, or part of it is bleeding into the airway and an obturator isolates the bleeding region and inhibits coughing which may damage the lung further, or at least cause further discomfort to the patient.

Figure 2:
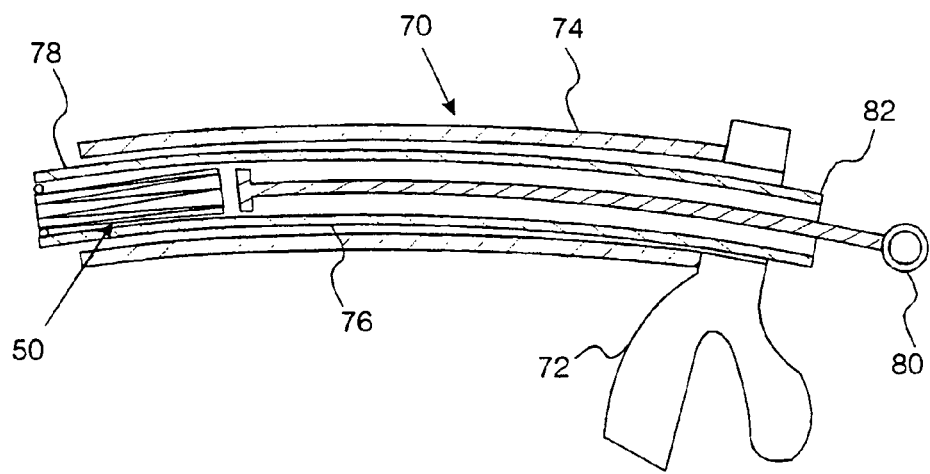
FIG. 2 shows a bronchial obturator complete with delivery system.

FIG. 2 shows an endo-bronchial obturator 50 complete with delivery device 70. The delivery device comprises a handle and flexible guide tube 74. Slidably received in the guide tube is a delivery tube 76 having the obturator 50 disposed at its distal end 78. A release means 80 is insertable in a proximal end 82 of the delivery tube 76 and by means of which the obturator 50 may be ejected from the end of the delivery tube. The guide tube is guided down the trachea and into the appropriate bronchus by means of guide lines (not shown) which enable the delivery system to be turned to follow the desired course. Optical guidance means may be included, or real-time X-ray or other monitoring methods may be employed to guide the surgeon. Once the end of the guide tube reaches the correct location, the delivery tube is inserted in the handle end of the delivery device 70, and then the release means 80 is pushed down the tube 76 to eject the obturator. The obturator is adapted to expand or be expanded, when ejected, to fill and block the tube or tubule in which it is inserted.

As can be seen from FIG. 3a, the obturator 50a in its first embodiment is comprised of two main components, a securing element in the form of a stent 90, and a blocking element in the form of a closed-cell, PVC foam plug 92.

The stent 90 is constructed from a plurality of legs 91 of surgical grade stainless steel wire welded together such that when extended the stent appears as a series 90b of connected 'W's, as shown in an unconnected disposition in FIG. 3c. Indeed, it is not essential that the final connection between ends 94, 96 be made to form a closed crown arrangement (as shown in FIG. 3a); it is equally effective merely to roll the stent 90b as indicated by arrows in FIG. 3c.

When the two ends of the stent are joined together, the stent 90 folds into a circular frame or crown, capable of encompassing the biocompatible block 92. The stent is constructed so as to be of a size slightly smaller (in its unstressed condition) than the block, so that its natural resilience squeezes the block slightly. On the other hand, the stent should be larger than the airway into which it is to be introduced so that it presses outwardly against the wall of the airway, and is incorporated into the mucosa of the air passage.

The legs 91 of the stent crown are fitted with both internal barbs 98 and external anchors 100. The barbs 98 embed themselves in the block 92 and secure the block to the stent 90. The anchors 100 are adapted to engage the walls of the patient's airways to hold the stent in position.

FIG. 4a shows an internal barb 98. The internal barb, also constructed from surgical quality stainless steel, is substantially straight and has a hook 99 at one end. The hooked end 99 is the point and means by which the barb is secured to the biocompatible block.

FIG. 4b shows an external anchor 100. The anchor, which is also constructed from surgical quality stainless steel, is again substantially straight and has a coil 101 at its end. A coil is used so that damage is not caused to the tissue of the airway in which the obturator is fitted, particularly if and when the obturator is removed.

The barbs and anchors are joined to the stent crown by a welded joint between two adjacent legs 91. Barbs can alternate with anchors at the same end of the stent, or one end can have all barbs, while the other end has all anchors. Both arrangements are shown in FIGS. 3a and c respectively.

A different embodiment of obturator 50b, also in accordance with the present invention, is shown in FIG. 3b in which surgical quality stainless steel wires are all welded together at a point 104 to form a domed stent 90bb. Legs 91b are alternately turned inwards to form barbs 98b, or outwards to form anchors 100b. Alternatively, all the legs could be anchors 100b, with interspersed shorter barbs 98bb, as one is shown in dashed lines in FIG. 3b.

The aforementioned obturators all rely on resilience of the steel to return the stent to its original shape once released from the delivery mechanism and so as to enable fitment in a narrower tubule than the unstressed size of the stent would otherwise allow. However, this requires prestressing the stent and keeping it stressed during delivery. Thus the present invention may find suitable application for memory metals, which only return to their original shape when some physical condition changes, for example, temperature rise or electrical current flow.

It is essential for the blocking device 92 to be comprised of a resiliently deformable material such as PVC foam as mentioned above. This enables the blocking device to be easily surrounded by the stent 90 and deformed into a compact structure, thereby enabling delivery of the block to its destination in the lung.

It is likewise essential that the block be capable of expanding and reforming into its original shape once deposited in the desired location in the lungs. It should be noted that the block is deformed and reformed in both an axial and a radial direction. It is the block 92 which seals a bronchial tube or tubule; mucous surrounds the block and forms a fluid tight seal. The presence of the stent around the block does not inhibit sealing in any way since the stent is essentially incorporated into the mucosa lining the airway.

Under compression, PVC foam has a high coefficient of friction which would prevent ejection from the delivery device as described above, if it was not surrounded by the stent 90, which offers a relatively low friction surface to the inside of delivery tube 76.

However, it is feasible that the block 92 could include a low friction surface to enable such ejection without the stent. Instead of the stent as described above, anchor means might be moulded in biocompatible plastics material as a crown, for example, on one end of the block, and either be adhered, fused or otherwise bound thereto.

The effectiveness of the device depends, to some extent, on the length of the block. Moreover, the block is required to be of a size which is both comfortable to the patient once expanded in the lung and which expands to completely obstruct the passage of air into the affected portions of the lung. The extended size of the block therefore ranges between 5 mm and 25 mm in length, and between 5 and 11 mm in diameter, depending on the size of the tube or tubule to be obturated.

Obturator 50c shown in FIG. 5, comprises a balloon 200, which is inflated after insertion and then detached. The balloon is captivated in an appropriate securing device such as stent 202. In this case, the barbs would not be sharp, but would merely retain ends of the balloon, or, as shown, would comprise turned-in points 204, 206 at each end of the stent. Anchors 201 are provided.

Finally, as mentioned above, the obturator may be as shown at 50d in FIG. 6, where it comprises a diaphragm 300 expanded by an internal stent 302 having anchors 302. One end 306 of the diaphragm is attached to the stent to retain it on the stent. The diaphragm is also adhered to the stent.

While the obturator and method of the present invention has been described with reference to human patients, animal patients may in certain circumstances also benefit.

The invention claimed is:

1. A method of treating an individual having an abnormal permanent enlargement of an airspace distal to a bronchial tube in a lung, said method comprising:
   providing a blocking element;
   inserting a delivery tube through airways of the individual to the bronchial tube of the individual, wherein the delivery tube is loaded with the blocking element;
   guiding the delivery tube to a suitable location within the bronchial tube; and
   releasing the blocking element in the bronchial tube, wherein the blocking element prohibits air from flowing through the bronchial tube into the airspace as the patient inhales and isolates the airspace supplied by the bronchial tube so that the airspace deflates over time as the air in the airspace becomes absorbed.

2. The method of claim 1, wherein the blocking element is inserted in the bronchial tube in a compressed state and expands into engagement with a wall of the bronchial tube.

3. The method of claim 2, wherein the blocking element expands into sealing engagement with the bronchial tube to form an air tight seal between the blocking element and a wall of the bronchial tube.

4. The method of claim 1, wherein the blocking element comprises a securing element that is expandable to a shape suitable for engaging a wall of the bronchial tube.

5. The method of claim 4, wherein the blocking element is inserted in the bronchial tube in a compressed state and expands into engagement with the wall of the bronchial tube.

6. The method of claim 4, wherein the securing element comprises a stent.

7. A method as in claim 6, wherein the stent is a self-expanding stent.

8. The method of claim 4, wherein the securing element comprises a memory metal which is released to an expanded shape by a change in a physical parameter after it has been inserted in the terminal bronchiole.

9. The method of claim 1, wherein the blocking element comprises a substantially cylindrical plug of biocompatible material.

10. The method of claim 9, wherein the plug comprises resiliently deformable closed-cell foamed plastics material.

11. The method of claim 1, wherein the blocking element comprises a balloon or a diaphragm.

12. The method of claim 1, wherein the blocking element is released by pushing the blocking element out of the delivery tube.

13. The method of claim 1, further comprising:
   providing a second blocking element;
   inserting the second blocking element in a second bronchial tube of the individual; and
   releasing the second blocking element in the second bronchial tube so that the second blocking element prohibits air from flowing through the second bronchial tube into a second airspace as the patient inhales and isolates the second airspace so that the second airspace deflates over time as the air in the second airspace becomes absorbed.

14. The method of claim 1, wherein the lung disease is emphysema.

15. A method of treating an individual having an abnormal permanent enlargement of an airspace distal to a bronchial tube in a lung, said method comprising:
   guiding a delivery tube to a suitable location within the bronchial tube of the individual;
   inserting a material from the delivery tube to the location in the bronchial tube so that the material prohibits air from flowing through the bronchial tube in both an inhalation direction and an exhalation direction; and
   releasing the material in the from the delivery tube in the bronchial tube so that air is trapped in the airspace distal to the terminal bronchiole and is absorbed over time.

16. A method as in claim 15, wherein the abnormal permanently enlarged airspace is caused by emphysema.

* * * * *

UNITED STATES PATENT AND TRADEMARK OFFICE
CERTIFICATE OF CORRECTION

| | |
|---|---|
| PATENT NO. | : 7,670,373 B1 |
| APPLICATION NO. | : 09/762692 |
| DATED | : March 2, 2010 |
| INVENTOR(S) | : Sabanathan |

Page 1 of 1

It is certified that error appears in the above-identified patent and that said Letters Patent is hereby corrected as shown below:

Col. 8, lines 25-32, Claim 15 should read

15. A method of treating an individual having an abnormal permanent enlargement of an airspace distal to a bronchial tube in a lung, said method comprising:

guiding a delivery tube to a suitable location within the bronchial tube of the individual;

inserting a material from the delivery tube to the location in the bronchial tube so that the material prohibits air from flowing through the bronchial tube in both an inhalation direction and an exhalation direction; and releasing the material from the delivery tube in the bronchial tube so that air is trapped in the airspace distal to the terminal bronchiole and is absorbed over time.

Signed and Sealed this

Seventeenth Day of August, 2010

David J. Kappos
*Director of the United States Patent and Trademark Office*